United States Patent
Forsberg

(10) Patent No.: US 6,635,047 B2
(45) Date of Patent: Oct. 21, 2003

(54) INTEGRATED POLYMER AND BRAID FOR INTRAVASCULAR CATHETERS

(75) Inventor: Andrew Forsberg, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/923,667

(22) Filed: Aug. 6, 2001

(65) Prior Publication Data

US 2003/0028173 A1 Feb. 6, 2003

(51) Int. Cl.[7] .......................... A61M 25/00; B29C 47/88
(52) U.S. Cl. .................. 604/526; 604/527; 604/525; 264/211.2; 264/345
(58) Field of Search .................. 604/264, 523, 604/524, 525, 526, 527, 528, 529, 282; 264/405, 641, 642, 6, 109, 112, 113, 125, 209.1, 211.12, 211.17, 211.14, 211.2, 345

(56) References Cited

U.S. PATENT DOCUMENTS

| | | |
|---|---|---|
| 4,495,134 A | 1/1985 | Ouchi et al. |
| 5,019,057 A | 5/1991 | Truckai |
| 5,057,092 A * | 10/1991 | Webster, Jr. ................. 138/123 |
| 5,176,660 A * | 1/1993 | Truckai ....................... 138/123 |
| 5,234,416 A * | 8/1993 | Macaulay et al. .......... 600/435 |
| 5,318,032 A | 6/1994 | Lonsbury et al. |
| 5,338,295 A | 8/1994 | Cornelius et al. |
| 5,885,207 A | 3/1999 | Iwasaka |
| 5,891,110 A | 4/1999 | Larson et al. |
| 6,004,310 A | 12/1999 | Bardsley et al. |
| 6,143,013 A * | 11/2000 | Samson et al. ............. 606/192 |
| 6,171,295 B1 * | 1/2001 | Garabedian et al. ........ 604/264 |
| 6,186,978 B1 | 2/2001 | Samson et al. |

* cited by examiner

Primary Examiner—Brian L. Casler
Assistant Examiner—Catherine Serke
(74) Attorney, Agent, or Firm—Crompton, Seager & Tufte, LLC

(57) ABSTRACT

An intravascular catheter including a reinforcement layer having a plurality of interwoven metal wire members and polymer members. The polymer members are thermally processed to permeate the metal wire members to form a polymeric layer having an orientation which is interwoven with the metal wire members.

14 Claims, 1 Drawing Sheet

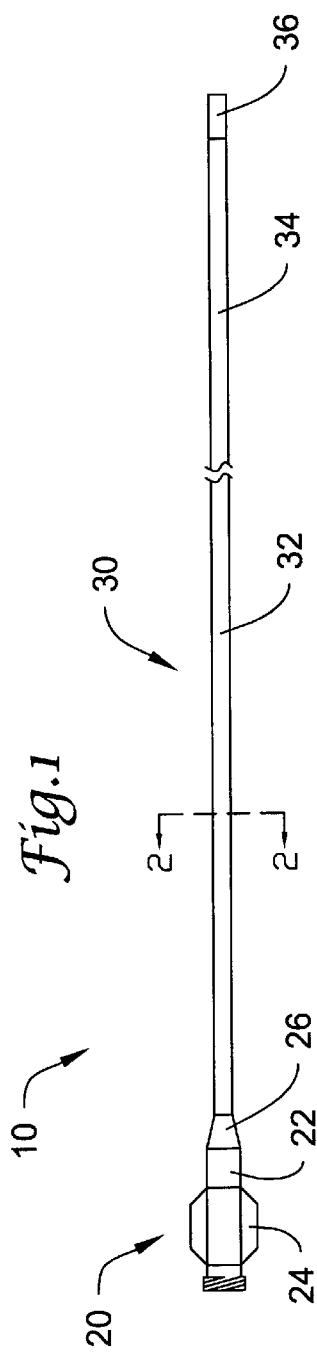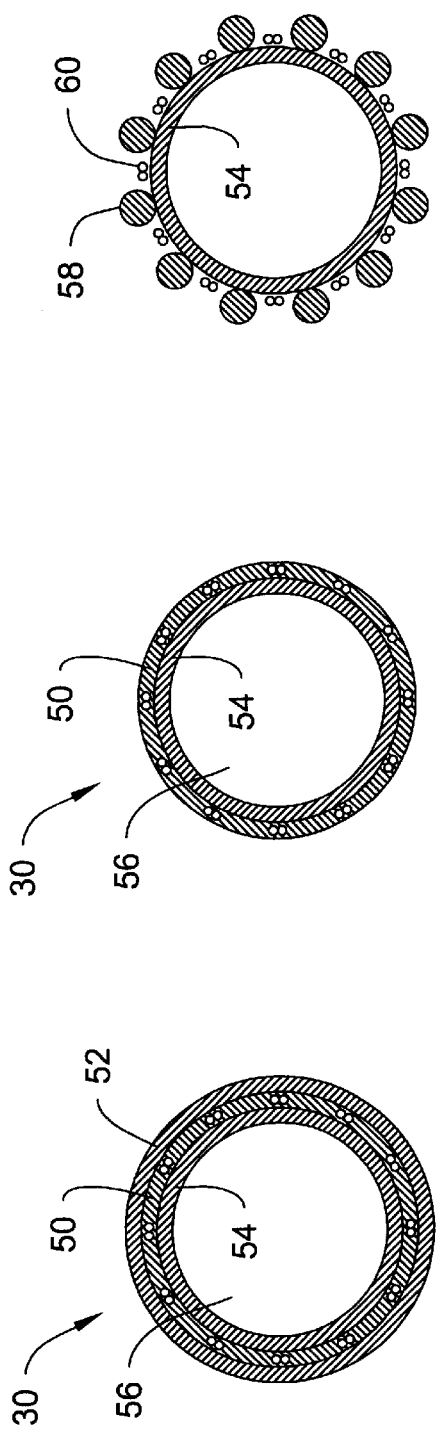

INTEGRATED POLYMER AND BRAID FOR INTRAVASCULAR CATHETERS

FIELD OF THE INVENTION

The present invention generally relates to intravascular devices. More specifically, the present invention relates to reinforced intravascular catheters.

BACKGROUND OF THE INVENTION

Intravascular catheters commonly comprise a polymer shaft having a braid reinforcement embedded therein. The prior art offers a number of different reinforced catheter designs and methods of manufacture, each of which have certain advantages and disadvantages. To address these disadvantages, there is an ongoing need to provide design alternatives for reinforced catheters.

SUMMARY OF THE INVENTION

To this end, the present invention provides several reinforced catheter designs and related methods of manufacture. For example, in one embodiment, the present invention provides an intravascular catheter including a reinforcement layer having a plurality of interwoven metal wire members and polymer members. The polymer members are thermally processed to permeate the metal wire members to form a polymeric layer having an orientation which is interwoven with the metal wire members.

BRIEF DESCRIPTION OF THE DRAWINGS

FIG. 1 is a plan view of an intravascular catheter in accordance with an embodiment of the present invention;

FIGS. 2A and 2B are cross-sectional views taken along line 2—2 in FIG. 1; and

FIG. 3 is a cross-sectional view taken along line 2—2 in FIG. 1, showing the reinforcement layer prior to thermal processing.

DETAILED DESCRIPTION OF THE INVENTION

The following detailed description should be read with reference to the drawings in which similar elements in different drawings are numbered the same. The detailed description and the drawings, which are not necessarily to scale, depict illustrative embodiments and are not intended to limit the scope of the invention.

Refer now to FIG. 1 which illustrates a plan view of an intravascular catheter 10 in accordance with an embodiment of the present invention. Intravascular catheter 10 may comprise a wide variety of intravascular catheters such as a coronary guide catheter as shown. However, those skilled in the art will recognize that the principles and concepts described herein may be applied to virtually any intravascular catheter including guide catheters, diagnostic catheters, balloon catheters, atherectomy catheters, etc. Except as described herein, the catheter 10 may be manufactured using conventional techniques and may be used in accordance with the intended clinical application.

In this particular example, the intravascular catheter 10 includes an elongate shaft 30 having a proximal end and a distal end. A hub and strain relief assembly 20 is connected to the proximal end of the elongate shaft 30. The hub and strain relief assembly 20 includes a main body portion 22, a pair of flanges 24 to facilitate gripping and manipulation of the catheter 10, and a strain relief 26 to reduce the likelihood of kinking between the relatively stiff body portion 22 and the relatively flexible shaft 30. The hub and strain relief assembly 20 may be of conventional design and may be connected to the proximal end of the elongate shaft 30 utilizing conventional techniques.

The elongate shaft 30 includes a proximal portion 32, a distal portion 34 and a distal tip 36. The proximal portion 32 and the distal portion 34 of the elongate shaft 30 may comprise a braid reinforced polymer tube which generally increases in flexibility toward the distal end of the elongate shaft 30. The distal tip 36 may comprise a polymer tube without braid reinforcement to render it soft and atraumatic and may be loaded with radiopaque material to render it radiopaque.

Refer now to FIGS. 2A and 2B which illustrate cross-sectional views of alternative embodiments of the elongate shaft 30 taken along line 2—2 in FIG. 1. The cross-sectional view of the elongate shaft 30 shown in FIGS. 2A and 2B is representative of the construction of the proximal 32 and distal 34 portions of the shaft 30 containing the braid reinforcement. The embodiment of FIG. 2A illustrates a tri-layer construction of the shaft 30, and the embodiment of FIG. 2B illustrates a dual-layer construction of the shaft 30.

With specific reference to FIG. 2A, this embodiment of the elongate shaft 30 includes an outer layer 52, an inner layer 54, and a reinforcement layer 50 disposed therebetween. With specific reference to FIG. 2B, this alternative embodiment of the elongate shaft 30 includes an inner layer 54 and a reinforcement layer 50 disposed thereon. The alternative embodiment of the shaft 30 illustrated in FIG. 2B is essentially the same as the embodiment illustrated in FIG. 2A except that the outer layer 52 is omitted.

The inner layer 54 defines a lumen 56 which extends through the entire length of the elongate shaft 30 to provide fluid communication the hub assembly 20. The inner layer 54 may comprise a lubricous polymeric tube or coating comprising a material such as PTFE having an inside diameter of approximately 0.053 to 0.107 inches and a wall thickness of approximately 0.0001 to 0.002 inches. The reinforcement layer 50 is disposed about the inner layer 54 and is described in more detail hereinafter.

The outer layer 52 may comprise a thermoplastic polymer such as a co-polyester thermoplastic elastomer (TPE) available under the tradename Arnitel®, or a polyether block amide (PEBA) available under the tradename PEBAX®. The outer layer 52 may have an inside diameter roughly corresponding to the outside diameter of the reinforcement layer 50 and a wall thickness of approximately 0.005 inches. As mentioned previously, the shaft 30 gradually decreases in stiffness toward the distal end thereof. The decrease in stiffness may be provided by varying the hardness (durometer) of the outer layer 52. This may be accomplished, for example, by utilizing a series of tubular polymer segments of decreasing hardness, or by utilizing an interrupted layer co-extrusion (ILC) process. The decrease in stiffness of the shaft 30 may also be provided by varying the stiffness of the reinforcement layer 50 as described in more detail hereinafter.

With reference to FIG. 3, the reinforcement layer 50 may comprise a plurality of polymer members 58 interwoven with a plurality of metal wires 60. The polymer members 58 are thermally processed to permeate the metal wire members 60 as shown in FIGS. 2A and 2B. The polymer members 58 may have a larger cross-sectional area, both individually and cumulatively, than the metal wire members 60 such that the polymer material of the polymer member 58 at least partially and preferably fully encases the metal wire members 60 post thermal processing.

The polymer members 58 may have a pic count per unit length (number of intersections per unit length) which varies along the length of the elongate shaft 30 to thereby vary the wall thickness of the reinforcement layer 50 and the elongate shaft 30. The polymer members 58 may have a durometer which varies along the length of the elongate shaft 30 to thereby vary the stiffness of the reinforcement layer 50 and the elongate shaft 30.

The polymer members 58 and the metal wire members 60 may be interwoven using conventional braiding machines. The polymer members 58 and the metal wire members 60 may be braided over a mandrel such as a PTFE covered copper wire mandrel, which may subsequently define the inner layer 54 upon removal of the copper wire mandrel.

After the polymer members 58 and the metal wire members 60 have been interwoven utilizing a braiding machine, a thermal process may be used to melt the polymer members 58 such that the polymer material thereof flows and permeates the metal wire members 60. For example, the braided subassembly 58/60 may be drawn through a heated die to melt the polymer members 58 and form a uniform outer surface as shown in FIG. 2B. Those skilled in the art will recognized that other suitable thermal processing may be used to achieve the same or similar result. The outer layer 52 may then be formed over the reinforcement layer 50 using conventional techniques.

The polymer material forming the polymer members 58 may be compatible with the polymer material forming the inner layer 54 and/or the outer layer 52 to establish thermal bonds therebetween. To this end, the polymer members 58 may comprise a thermoplastic polymer. Alternatively, the polymer members 58 may comprise a thermosetpolymer which is curved after forming.

The polymer members 58 may be formed by a conventional extrusion process to have a constant diameter and durometer to thereby form a reinforcement layer 50 having a constant wall thickness and stiffness. Alternatively, the polymer members 58 may be formed by an extrusion process wherein the diameter and/or the durometer changes such that the wall thickness and/or stiffness of the reinforcement layer 50 also changes. As an alternative, the polymer members 58 may comprise a polymer material surrounding a metal or fibrous core material (e.g., stainless steel, carbon fiber, aramid fiber, etc.) to facilitate better braiding and to enhance the strength of ht reinforcement layer 50.

The braiding process may also be adjusted to vary the pic count of the polymer member 58 and/or the metal wire members 60 to thereby vary the stiffness and wall thickness of the reinforcement layer 50. In particular, as the pic count per unit length of the polymer members 58 decreases, the wall thickness and the stiffness of the reinforcement layer 50 decreases. Conversely, as the pic count per unit length of the polymer members 58 increases, the wall thickness and stiffness of the reinforcement layer 50 also increases.

By braiding the polymer members 58 with the wire members 60, followed by thermal processing to permit the polymer members 58 to permeate the metal wire members 60, the polymer material of the reinforcement layer 50 forms an orientation which is interwoven with the metal wire members. Although the polymer members 58 are preferably interwoven with the wire members 60, it is also contemplated that the polymer members 58 may be braided over or under the braided wire members 60.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular catheter comprising an elongate shaft including a reinforcement layer having a plurality of interwoven metal wire members and polymer members, wherein the polymer members are thermally processed to permeate the metal wire members and wherein the elongate shaft has a length and a wall thickness, and wherein the polymer members have a pic count per unit length which varies along the length of the elongate shaft to thereby vary the wall thickness thereof, and wherein the polymer members have a larger cross-sectional area than the metal wire members.

2. An intravascular catheter as in claim 1, wherein the polymer members have a cumulative cross-sectional area sufficient to at least partially encase the metal wire members.

3. An intravascular catheter as in claim 1, wherein the polymer members have a cumulative cross-sectional area sufficient to fully encase the metal wire members.

4. An intravascular catheter as in claim 1, wherein the elongate shaft has a length and a stiffness, and wherein the polymer members have a durometer which varies along the length of the elongate shaft to thereby vary the stiffness thereof.

5. An intravascular catheter as in claim 1, further comprising an inner polymeric layer defining a lumen extending therethrough, with the reinforcement layer covering the inner polymeric layer.

6. An intravascular catheter as in claim 5, further comprising an outer polymeric layer covering the reinforcement layer.

7. An intravascular catheter as in claim 6, wherein the polymer members thermally fuse to the outer polymer layer.

8. An intravascular catheter as in claim 6, wherein the polymer members and the outer polymeric layer comprise thermally bondable polymeric materials.

9. An intravascular catheter as in claim 8, wherein the polymer members and the outer polymeric layer comprise the same polymeric material.

10. A method of making an intravascular catheter, comprising:

braiding a plurality of metal wire members with a plurality of polymer members; and thermally processing the polymer members to permeate the metal wire members;

wherein the catheter has a length and a wall thickness, and wherein the polymer members are braided to have a pic count per unit length that varies to thereby vary the wall thickness, and wherein the polymer members are extruded to have a durometer which varies to thereby vary a stiffness of the catheter.

11. A method of making an intravascular catheter as in claim 10, wherein the polymer members have a cumulative cross-sectional area sufficient to at least partially encase the metal wire members after thermal processing.

12. A method of making an intravascular catheter as in claim 10, wherein the polymer members have a cumulative cross-sectional area sufficient to fully encase the metal wire members after thermal processing.

13. A method of making an intravascular catheter as in claim 10, further comprising the act of forming an inner polymeric layer and braiding the reinforcement layer thereon.

14. A method of making an intravascular catheter as in claim 13, further comprising the step of forming an outer polymeric layer over the reinforcement layer.

* * * * *